United States Patent [19]

Adey et al.

[11] Patent Number: 4,471,149

[45] Date of Patent: Sep. 11, 1984

[54] PROCESS FOR THE ORTHO-ALKYLATION OF PHENOLS

[75] Inventors: Kenneth A. Adey, Kempsey; Frank S. Yates, Brocton; John H. Young, Dunston Heath, all of England

[73] Assignee: Croda Synthetic Chemicals Limited, Goole, England

[21] Appl. No.: 493,407

[22] Filed: May 11, 1983

Related U.S. Application Data

[63] Continuation-in-part of Ser. No. 308,730, Oct. 5, 1981, Pat. No. 4,386,226.

[30] Foreign Application Priority Data

Oct. 14, 1980 [GB] United Kingdom ............... 8033114
Mar. 7, 1981 [GB] United Kingdom ............... 8107218

[51] Int. Cl.$^3$ .................................... C07C 37/16
[52] U.S. Cl. .................................... 568/804; 568/794
[58] Field of Search .......................... 568/804, 794

[56] References Cited

U.S. PATENT DOCUMENTS

| | | | |
|---|---|---|---|
| 3,923,907 | 12/1975 | Kotingawa et al. | 568/804 |
| 3,953,529 | 4/1976 | Yonemitsu et al. | 568/804 |
| 4,227,024 | 10/1980 | Leach | 568/804 |
| 4,386,226 | 5/1983 | Adey et al. | 568/804 |

FOREIGN PATENT DOCUMENTS

| | | | |
|---|---|---|---|
| 0081647 | 10/1982 | European Pat. Off. | 568/804 |
| 49236 | 5/1975 | Japan | 568/804 |
| 0035061 | 9/1978 | Japan | 568/804 |
| 1124839 | 8/1968 | United Kingdom | 568/804 |

*Primary Examiner*—Werren B. Lone
*Attorney, Agent, or Firm*—Lawrence Rosen

[57] ABSTRACT

A phenol is ortho-alkylated by reaction with an alkanol in the presence of a catalyst comprising at least 92% w/w, calculated as $Fe_2O_3$, of an oxide of iron, and at least one other metal oxide. By way of example, phenol can thus be converted to o-cresol and/or 2,6-xylenol.

8 Claims, No Drawings

PROCESS FOR THE ORTHO-ALKYLATION OF PHENOLS

RELATIONSHIP TO EARLIER APPLICATION

This application is a continuation-in-part of our earlier application, Ser. No. 308,730, filed Oct. 5, 1981 now U.S. Pat. No. 4,386,226.

PRIOR ART

It is well known to react a phenol which is unsubstituted at at least one ortho position with an alkanol in the presence of a catalyst. Such a reaction is used, for example, to prepare o-cresol (e.g., for herbicide manufacture), 2,6-xylenol (e.g., for the manufacture of polyphenylene ether) and 2,3,6-trimethylphenol (e.g., for vitamin E manufacture).

Many catalysts for the ortho-alkylation of phenols are known. British Patent Specification No. 602,257 discloses alumina as catalyst, and a reaction temperature of 345° C., but appreciable quantities of phenol remain unreacted and meta- and para-alkylation products are formed in substantial amounts. U.S. Pat. No. 3,843,606 discloses magnesia as the catalyst and reports somewhat higher conversion of the phenol feedstock, and relatively high selectivities, but requires the temperature of operation to be in excess of 400° C., e.g. 460° C.

It is known to use iron oxide as a component of a catalyst for use in the ortho-alkylation of phenols. U.S. Pat. No. 3,716,589 discloses such a catalyst, containing oxides of iron and another metal (M) in sufficient amounts to form a spinel of the formula $MFe_2O_4$. By conducting the alkylation reaction with this catalyst at about 350° C., high selectivity to ortho-alkylation is achieved but, with quoted conversions not exceeding 71%, a major proportion of the phenol feedstock must be recycled.

Other references which disclose ortho-alkylation catalysts include British Patent Specification No. 1,378,179 where the catalyst comprises oxides of iron, vanadium and a further metal. British Patent Specification No. 1,428,057 discloses a catalyst comprising oxides of iron and silicon.

C.A. 77:101173d discloses a catalyst comprising vanadium and iron oxides in comparable amounts and another metal oxide. C.A. 78:3944g discloses a catalyst comprising a mixture of indium and iron oxides. C.A. 79:78384d discloses a catalyst comprising a spinel of the formula $MFe_2O_4$ in which M is barium, calcium, magnesium or a transition metal.

C.A. 81:105003d discloses a catalyst comprising iron oxide and nickel oxide in which the Ni:Fe molar ratio is 1:2. C.A. 82:155769z discloses a catalyst comprising manganese and iron oxides, optionally together with cobalt oxide. C.A. 84:58898z discloses a catalyst of the formula $Zn_2Fe_2Mo_{0.03}O_4$.

C.A. 90:6086n discloses a catalyst of the formula $MFe_2O_4$ in which M is Mg, Ca, Ba, Cu, Ni, Cr, Co or Cu-Zn. C.A. 93:71286d discloses a catalyst comprising a mixture of the oxides of Fe, Cr, Sb, V and Si.

C.A. 94:103010y discloses a catalyst comprising oxides of iron and one of Mo, Sn, W and Zr. In the given example, the catalyst comprises Fe and Zr in an atomic ratio of 96:4.

European Patent Publication No. 19476, published Nov. 26, 1980, discloses a catalyst comprising a major proportion of an iron oxide and a minor propostion of an oxide of a metal selected from Ga, Ge, Y, Nd, Hf, Bi and Ta. Examples 45, 46, 49 and 50 of this Publication disclose catalysts comprising three metal oxides, of iron, germanium and either Zr or Sn, in a metal atom ratio of 97:1.8:1.2.

It will thus be apparent that a wide variety of mixtures of metal compounds has been proposed for use as catalysts in the ortho-alkylation of phenols. It is difficult to make any clear inference as to the most suitable catalyst for use in this reaction.

OBJECT OF THE INVENTION

An object of the invention is to provide an industrially-applicable process for the production of o-alkylphenols.

DESCRIPTION OF THE INVENTION

According to the present invention, a catalyst which is used in the reaction of a phenol with an alkanol to form an o-alkylphenol, comprises an oxide of iron and at least one other metal oxide.

The catalyst used in the present invention comprises a major proportion of an iron oxide. The catalyst will suitably be prepared from $Fe_2O_3$, although any suitable form of iron oxide is appropriate. In use, $Fe_2O_3$ may be converted to $Fe_3O_4$.

The oxide of the metal in the catalyst other than iron may be of Group II of the Periodic Table (Cd, Hg), Group III (Sc, In or a lanthanide, At. No. 57-71, such as Ce), Group IV (Pb, Sn, Ti or Zr), Group V (As) or Group VIII (Co or Ni). If desired, the catalyst may be prepared from a salt or other compound of the desired metal which is converted to the oxide during preparation or in use of the catalyst.

The amount of iron oxide in the catalyst, calculated as $Fe_2O_3$, is usually at least 92% w/w. The amount of the metal other than iron in the catalyst, calculated as its oxide, will usually be at least 0.5% w/w and is preferably no more than 8, more preferably no more than 5, and most preferably no more than 3, % w/w. The preferred amount is about 1% w/w (here and throughout the specification, percentages of components in the catalyst are measured on the basis of the dry weight of the component with respect to the total weight of the catalyst).

The catalyst may comprise an oxide of a metal other than iron which is not detrimental to the reaction, usually in an amount of no more than 5% w/w.

It is often preferred that the catalyst should comprise $Cr_2O_3$ in an amount of up to 5% w/w. It is also preferred that the catalyst should comprise an alkali metal oxide or salt, e.g. of Na or K. A suitable such compound is $K_2CO_3$. The amount of any such alkali metal compound may be up to 5% w/w.

The catalyst may be prepared by conventional means. It may be produced in any form which is appropriate for a vapour-phase reaction.

The phenol feedstock may be any phenol which is unsubstituted at at least one ortho position. The feedstock may be, for example, phenol or m-cresol. The alkanol is preferably a $C_{1-4}$ alkanol and is most preferably methanol or ethanol. By the process of the invention, phenol may be reacted with methanol to give o-cresol and/or 2,6-xylenol, and m-cresol may be reacted with methanol to give 2,3,6-trimethylphenol.

The alcohol is usually present in excess. Water is usually included in the alkanol/phenol feedstock, to extend the life of the catalyst.

The temperature of the reaction is usually from 300° to 500° C., preferably from 320° to 420° C., and often about 330° to 360° C. The reaction may be carried out in fluidised or fixed bed equipment. The pressure is not especially critical but it will often be appropriate to conduct the reaction at atmospheric or slightly superatmospheric pressure.

The process may be conducted using liquid hourly space velocities of, for example, 0.3 to 3 liters of liquid feed per liter of catalyst per hour. This rate is often less than 1.0 when di-alkylation is required, and rather higher when appreciable amounts of mono-alkylation are desired.

The preparation of catalysts for use in, and the process of, the invention will now be given, together with comparative data. All parts and percentages are by weight, unless otherwise specified.

Catalyst Composition A 600 parts of ferric nitrate ($Fe(NO_3)_3.9H_2O$) and 3.82 parts of chromic nitrate ($Cr(NO_3)_3.9H_2O$) were dissolved in 6000 parts of water. To this solution were added 4.21 parts of zirconium nitrate ($Zr(NO_3)_4.5H_2O$) in the form of a 10% solution in water. Dilute aqueous ammonia was then added with stirring until the solution was neutral. After a period of ageing, the resultant hydrogel was recovered by filtration, washed, and dried for 10 hours at 180° C. It was then soaked overnight in a solution containing 0.048 parts of potassium carbonate, re-dried and calcined for 4½ hours in air at 470° C., before being formed into 3.1 mm pellets.

Catalyst Compositions B to K

In a similar way to the production of catalyst A, but using different amounts of zirconium nitrate, catalysts B, C and D were prepared. In a similar way, instead of using zirconium nitrate, solutions of titanium tetrachloride, lead nitrate, cadmium nitrate, stannic chloride, cerium nitrate, nickel nitrate and cobalt nitrate were used to prepare catalysts E, F, G, H, I, J and K, respectively.

Catalysts A to K have the following compositions, on a dry weight basis, the balance of each composition being $Fe_2O_3$:

| | | | |
|---|---|---|---|
| A | 1% $ZrO_2$ | 0.6% $Cr_2O_3$ | 0.04% $K_2CO_3$ |
| B | 2% $ZrO_2$ | 0.6% $Cr_2O_3$ | 0.04% $K_2CO_3$ |
| C | 3% $ZrO_2$ | 0.6% $Cr_2O_3$ | 0.04% $K_2CO_3$ |
| D | 10% $ZrO_2$ | 0.6% $Cr_2O_3$ | 0.04% $K_2CO_3$ |
| E | 1% $TiO_2$ | 0.6% $Cr_2O_3$ | 0.04% $K_2CO_3$ |
| F | 1% PbO | 0.6% $Cr_2O_3$ | 0.04% $K_2CO_3$ |
| G | 1% CdO | 1.1% $Cr_2O_3$ | 0.05% $K_2CO_3$ |
| H | 1.2% $SnO_2$ | 0.9% $Cr_2O_3$ | 0.02% $K_2CO_3$ |
| I | 1% $CeO_2$ | 0.6% $Cr_2O_3$ | 0.04% $K_2CO_3$ |
| J | 1% NiO | 0.6% $Cr_2O_3$ | 0.04% $K_2CO_3$ |
| K | 1% CoO | 0.6% $Cr_2O_3$ | 0.04% $K_2CO_3$ |

60 ml of each of catalysts A to K were packed in a mild steel reaction tube and maintained at a background temperature of 345° C. A gaseous mixture of methanol, phenol and water at a molar ratio of 5:1:1 was passed through the catalyst bed at a liquid hourly space velocity (LHSV) of 0.4 or 0.6 kg of liquid feed/l catalyst/hr. The results which were obtained are tabulated below.

The use of catalysts A, B, C, E and G illustrates the process claimed in the patent to be issued on our Application Ser. No. 308,730, filed Oct. 5, 1981. The use of catalyst D shows that relatively poor results are obtained when the proportion of the metal oxide other than iron oxide is increased.

The use of catalysts F and H is comparative. The use of catalysts I, J and K illustrates the present invention.

| Catalyst | A | B | C | D | E | F | G | G | H | I | J | K |
|---|---|---|---|---|---|---|---|---|---|---|---|---|
| L H S V | 0.4 | 0.4 | 0.4 | 0.4 | 0.4 | 0.4 | 0.4 | 0.6 | 0.6 | 0.6 | 0.6 | 0.6 |
| Liquid product recovery % | 77.2 | 78.9 | 87.5 | 83.7 | 81.8 | 80.4 | 51.4 | 55 | 82.0 | 73.2 | 79.2 | 68.1 |
| Phenol conversion % | 94.3 | 98.9 | 59.7 | 54.2 | 98.9 | 67.6 | 100 | 96.0 | 93.4 | 97.5 | 97.5 | 97.8 |
| Selectivity to 2,6-xylenol % | 69.1 | 82.1 | 23.7 | 15.0 | 81.5 | 20.9 | 89.4 | 66.9 | 66.0 | 72.1 | 76.5 | 72.7 |
| Selectivity to o-cresol % | 28.6 | 16.0 | 71.2 | 77.4 | 12.7 | 76.8 | 6.8 | 30.3 | 31.9 | 25.1 | 22.3 | 25.3 |
| Selectivity to o-methylation % | 97.7 | 98.1 | 94.9 | 92.4 | 94.2 | 97.7 | 96.2 | 97.2 | 97.9 | 97.2 | 98.8 | 98.0 |
| Selectivity to others % | 2.3 | 1.9 | 5.0 | 7.0 | 5.8 | 1.6 | 3.8 | 2.8 | 2.0 | 2.8 | 1.1 | 1.9 |

We claim:

1. A process for preparing an o-alkylphenol, which comprises reacting at a temperature of 300°–500° C. a monohydric phenol unsubstituted at at least one ortho position, with a $C_{1-4}$ alkanol, in the presence of a catalyst comprising at least 92% w/w, calculated as $Fe_2O_3$, of an oxide of iron, and 0.5–3% w/w of an oxide of another metal which is selected from Ce, Co and Ni.

2. A process according to claim 1, which is conducted at from 320° to 420° C.

3. A process according to claim 1, in which the alkanol is methanol.

4. A process according to claim 1, in which the catalyst additionally comprises $Cr_2O_3$, in an amount of up to 5% w/w.

5. A process according to claim 1, in which the catalyst additionally comprises an alkali metal compound, in an amount of up to 3% w/w.

6. A process according to claim 1, in which the said other metal oxide is CoO.

7. A process according to claim 1, in which the said other metal oxide is NiO.

8. A process for preparing an o-alkylphenol, which comprises reacting at a temperature of 300°–500° C. a monohydric phenol unsubstituted at at least one ortho position, with methanol, in the presence of a catalyst comprising at least 92% w/w, calculated as $Fe_2O_3$, of an oxide of iron, up to 5% w/w $Cr_2O_3$, and 0.5–3% w/w of cerium oxide.

* * * * *